US012728215B2

(12) United States Patent
Tweedie et al.

(10) Patent No.: US 12,728,215 B2
(45) Date of Patent: Sep. 8, 2026

(54) POWDER INHALER ASSEMBLY

(71) Applicant: CHIESI FARMACEUTICI S.P.A., Parma (IT)

(72) Inventors: Alan Tweedie, Parma (IT); Colin Mitchell, Parma (IT); Alan Sanders, Parma (IT); Andrew T. Heidt, Parma (IT); György Szarka, Parma (IT); Bogdan-Alexandru Cociu, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 1067 days.

(21) Appl. No.: 17/780,499

(22) PCT Filed: Nov. 27, 2020

(86) PCT No.: PCT/EP2020/083751
§ 371 (c)(1),
(2) Date: May 26, 2022

(87) PCT Pub. No.: WO2021/105440
PCT Pub. Date: Jun. 3, 2021

(65) Prior Publication Data

US 2023/0016850 A1 Jan. 19, 2023

(30) Foreign Application Priority Data

Nov. 28, 2019 (EP) .................................... 19212202

(51) Int. Cl.
*A61M 15/00* (2006.01)

(52) U.S. Cl.
CPC .... *A61M 15/0065* (2013.01); *A61M 15/0021* (2014.02); *A61M 15/0091* (2013.01); *A61M 2205/3306* (2013.01)

(58) Field of Classification Search
CPC .......... A61M 15/0065; A61M 15/0021; A61M 15/0091; A61M 2205/3306;
(Continued)

(56) References Cited

U.S. PATENT DOCUMENTS

| | | |
|---|---|---|
| 5,505,195 A | 4/1996 | Wolf et al. |
| 5,657,748 A | 8/1997 | Braithwaite |

(Continued)

FOREIGN PATENT DOCUMENTS

| | | |
|---|---|---|
| EP | 2119465 A1 | 11/2009 |
| EP | 2414978 A1 | 2/2012 |

(Continued)

OTHER PUBLICATIONS

Office Action for JP Application No. 2022-527971 Mail Date: Jun. 18, 2024 (Machine Translation and Original). 12 Pages.

(Continued)

*Primary Examiner* — Brandy S Lee
*Assistant Examiner* — Kris Hanyu Gong
(74) *Attorney, Agent, or Firm* — Steinfl + Bruno LLP

(57) ABSTRACT

A powder inhaler assembly includes a powder inhaler including a metering device having a dosing recess and movable, with respect to a container and to an inhalation channel, between an idle state, in which the dosing recess is in communication with an opening of the container so as to be filled with a dose of the powdered medicament, and a triggered state, in which the dosing recess is in communication with the inhalation channel for enabling inhalation of a dose of the powdered medicament contained in the dosing recess through a mouthpiece. An electronic module is attachable to the powder inhaler and includes a non-contact sensor positioned and configured to sense position(s) of at least part of the metering device to detect at least when the metering device is in the triggered state.

20 Claims, 9 Drawing Sheets

(58) Field of Classification Search
CPC ........ A61M 15/008; A61M 2205/3317; A61M 2205/3592; A61M 2205/505; A61M 2205/52; A61M 2205/583; A61M 15/0026; A61M 2202/064; A61M 2205/8206; A61M 15/0068; A61M 2205/587; H02J 7/0063; H02J 2310/23
See application file for complete search history.

(56) References Cited

U.S. PATENT DOCUMENTS

| | | | | |
|---|---|---|---|---|
| 5,809,997 | A * | 9/1998 | Wolf | A61M 15/0005 128/200.23 |
| 6,182,655 | B1 | 2/2001 | Keller et al. | |
| 6,377,848 | B1 | 4/2002 | Garde et al. | |
| 11,000,653 | B2 * | 5/2021 | Calderon Oliveras | A61B 5/4833 |
| 11,660,409 | B2 | 5/2023 | Tweedie et al. | |
| 2005/0028815 | A1 | 2/2005 | Deaton et al. | |
| 2005/0251289 | A1 | 11/2005 | Bonney et al. | |
| 2009/0114219 | A1 | 5/2009 | Ferris et al. | |
| 2014/0000603 | A1 | 1/2014 | Hosemann et al. | |
| 2014/0158126 | A1 * | 6/2014 | Parry-Billings | A61M 15/0026 128/203.15 |
| 2018/0070634 | A1 | 3/2018 | Sur et al. | |
| 2018/0140788 | A1 | 5/2018 | Calderon Oliveras et al. | |
| 2018/0348075 | A1 | 12/2018 | Rubinstein et al. | |
| 2019/0117919 | A1 | 4/2019 | Panarello et al. | |
| 2022/0218920 | A1 | 7/2022 | Roche et al. | |
| 2022/0305220 | A1 * | 9/2022 | Fato | A61M 15/0023 |
| 2023/0001111 | A1 | 1/2023 | Tweedie et al. | |

FOREIGN PATENT DOCUMENTS

| | | | | |
|---|---|---|---|---|
| EP | 3113817 | A1 | 1/2017 | |
| EP | 3501584 | A1 | 6/2019 | |
| JP | H9508845 | A | 6/1996 | |
| JP | 2018501079 | A | 1/2018 | |
| KR | 20180103924 | A | 9/2018 | |
| WO | 96/16686 | A1 | 6/1996 | |
| WO | WO-0236190 | A2 * | 5/2002 | A61M 15/008 |
| WO | 03/092576 | A2 | 11/2003 | |
| WO | 2004/012801 | A1 | 2/2004 | |
| WO | 2010/114392 | A1 | 10/2010 | |
| WO | 2014/150247 | A1 | 9/2014 | |
| WO | 2015/133909 | A1 | 9/2015 | |
| WO | 2016/000983 | A1 | 1/2016 | |
| WO | 2016/111633 | A1 | 7/2016 | |
| WO | WO-2016122927 | A1 * | 8/2016 | G06F 3/017 |
| WO | 2017/129521 | A1 | 8/2017 | |
| WO | 2017/178865 | A1 | 10/2017 | |
| WO | 2019/021254 | A1 | 1/2019 | |
| WO | WO-2021022118 | A1 * | 2/2021 | A61M 16/0003 |
| WO | 2021/105445 | A1 | 6/2021 | |

OTHER PUBLICATIONS

Non-Final Office Action issued by the USPTO for U.S. Appl. No. 17/780,503, Mail Date: Dec. 23, 2022, 9 pages.
Notice of Allowance for U.S. Appl. No. 17/780,503, filed May 26, 2022, on behalf of Chiesi Farmaceutici S.P.A., Mail Date: Apr. 4, 2023, 10 Pages.
International Search Report and Written Opinion for International Application No. PCT/EP2020/083751 filed on Nov. 27, 2020 on behalf of Chiesti Farmaceutici S.P.A. Mail Date: Dec. 22, 2020, 17 pages.
International Search Report and Written Opinion for International Application No. PCT/EP2020/083759 filed on Nov. 27, 2020 on behalf of Chiesti Farmaceutici S.P.A. Mail Date: Jan. 20, 2021, 14 pages.
Korean Office Action issued for KR Application No. 10-2022-7018765 filed on Jun. 2, 2022 on behalf of Chiesi Farmaceutici S.P.A. Mail Date: Sep. 18, 2025. (English translation and Original) 22 Pages.

* cited by examiner 1
5
2
4
36
24
3

6
1
7
5
2
4
24
36
3

14
21
20
13
23
28
27
29

X-X
16
13
19
11
17
21
20
14
18
Y-Y

X-X
16
19
13
17
14
22
21
Y-Y
18
20

POWDER INHALER ASSEMBLY

CROSS-REFERENCE TO RELATED APPLICATIONS

The present application is the U. S. National Stage of International Patent Application No. PCT/EP2020/083751 filed on Nov. 27, 2020 which, in turn, claims priority to European Patent Application No. 19212202.6 filed on Nov. 28, 2019.

TECHNICAL FIELD OF THE INVENTION

The present invention relates a powder inhaler assembly, i.e. a device for dispensing a powdered medicament preparation by inhalation. The device is in particular a portable, multiple-dose, breath activated dry powder inhaler without propellant gas, equipped with a metering device which dispenses doses from a medicament container. The device is in particular a portable multiple-dose dry powder inhaler equipped with a detachable electronic module configured to detect activation of the metering device and, possibly, other related functions.

BACKGROUND ART

The administering of a powdered medicament preparation by inhalation from an inhaler is commonly known. Multiple-dose type powder inhalers comprising a powder container and a metering member which measures and dispenses a unit dose are also known.

Document WO 2004/012801, by the same Applicant, discloses a powder inhaler comprising a container for storing a powdered medicament, a metering member having a dosing recess to be filled with a dose of the powdered medicament and a mouthpiece in communication with an inhalation channel of the powder inhaler. The powder inhaler comprises a protective member which is slidingly moveable on the metering member between a closed position, in which the protective member covers the dosing recess of the metering member if the metering member is in an inhalation position, and an open position, in which the protective member exposes the dosing recess thereby enabling inhalation of the dose of the powdered medicament contained in the dosing recess. The protective member is coupled to an inhalation actuated mechanism in such a manner that the inhalation actuated mechanism moves the protective member from its closed position to its open position if there is an inhalation suction force exerted by a user which exceeds a predetermined level. The mechanical structure of the powder inhaler of WO 2004/012801 is able to provide a powder inhaler with an improved dosing ability, whereby unintended dosing can be avoided. Nowadays every user owns an electronic device, such as a computer, a smartphone or a tablet, with applications which could be used in everyday life and which could be useful to manage administering of medicaments. Document WO 2016/000983, by the same Applicant, discloses a powder inhaler similar to the one of WO 2004/012801.

The powder inhaler of WO 2004/012801 and of WO 2016/000983 do not comprise any electronic device to interface with an external electronic device. Inhalers provided with electronic devices configured to detect actuation of the inhaler itself and/or to collect data are also known.

Document U.S. Pat. No. 6,182,655 discloses an inhaler for multiple dosed administration of a pharmacological dry powder consisting externally of a housing and of a protective cap which can be removed from a mouthpiece fitted on the housing. Arranged on the inside there are a slide rail, a dosing slide, a shutter, a carriage, a funnel arrangement, a counter device, a valve shield and a valve guide. Removal of the protective cap initiates the dosing, with a dose received in the dosing cavity being transported to the mouthpiece by means of the dosing slide. The inhaler can be supplemented with a plug-in, re-usable electronic module and a controllable nozzle so that data relevant to inhalation can be recorded and the flow conditions regulated. To measure the parameters, use is made of membrane/bending beam technology or a piezoresistive element in combination with a diaphragm or in combination with the Venturi measurement principle. To monitor the inhalation procedure, a mechanically and/or electronically generated acoustic and/or optical signal may be emitted on completion of a successful or unsuccessful inhalation.

Document U.S. Pat. No. 6,182,655 does not disclose in details the structure of the re-usable electronic module and the way such module monitors the inhalation procedure. Furthermore, the used sensors are configured to sense an air flow and are not reliable and fault proof.

Document U.S. Pat. No. 5,505,195 discloses a dry powder inhalant device adapted for mounting on a conventional medication dry powder dispenser having a mouthpiece incorporated in one end of the dispenser. The device is designed for monitoring prescribed dosages of dry powder medication received through the mouthpiece, the lips and into the mouth, throat, and respiratory system of a user of the device. The device includes an electronic housing mounted on the dispenser for computing and recording when a proper amount of dry powder is released inside the dispenser, when a proper amount of airflow is inhaled through the dispenser for mixing with the dry powder and when each dispenser or dry powder container is removed and replaced on the electronic housing.

Document U.S. Pat. No. 5,505,195 detects dispensing of medicament through a thermistor, a pressure device or an audio element device to detect airflow of the inhalation by the user. These sensors are not reliable and fault proof. Furthermore, the structure of the dry powder inhalant device of U.S. Pat. No. 5,505,195 is not able to prevent unintended dosing as WO 2004/01280 does.

Document WO2015/133909 discloses a compliance monitor for monitoring patient usage of a dry powder medicament delivery device. The medicament delivery device includes a store of medicament housed within a main body portion and a base portion which is rotatable with respect to the main body portion. The medicament delivery device also includes a medicament dispensing means for dispensing a dose of medicament into an inhalation chamber, a mouthpiece through which the dose of medicament may be inhaled by a user and a replaceable cap. The compliance monitor includes a first portion for receiving and/or retaining the base portion of the medicament delivery device and a second portion for releasably securing the medicament delivery device to the first portion. The compliance monitor may further include an electronics control module, the electronics control module being adapted to monitor and/or manipulate and/or store and/or transmit all compliance data gathered, relating to the patient usage of the medicament delivery device. An optical dose detector may be utilized for detecting rotation of the base portion with respect to the main body portion.

Also the structure of the dry powder inhalant device of WO2015/133909 is not able to prevent unintended dosing as WO 2004/01280 does.

Summary

It is an object of the present invention to eliminate the above drawbacks of hitherto known powder inhalers and to provide a powder inhaler with an improved electronic detection of medicament dosing.

In particular, it is an object of the present invention to provide a powder inhaler assembly provided with an electronic module which is able to detect movement of mechanical parts of the powder inhaler to infer medicament dosing in safe and reliable way.

It is also object of the present invention to provide an electronic module which is able to read the movements of such mechanical parts of the powder inhaler without imparting relevant structural modification to existing powder inhalers, like, for instance, the one disclosed in WO 2004/012801 or WO 2016/000983 of the same Applicant.

At least one of the above objects is substantially achieved by an assembly, an electronic module and a powder inhaler according to one or more of the appended claims and/or of the following aspects.

Aspects of the invention are disclosed in the following.

In accordance with a 1$^{st}$ independent aspect, a powder inhaler assembly, comprises:

- a powder inhaler comprising:
  - a container for storing a powdered medicament;
  - a mouthpiece and an inhalation channel connected to the mouthpiece;
  - a metering device having a dosing recess; wherein the metering device is movable, with respect to the container and the inhalation channel, between an idle state, in which the dosing recess is in communication with an opening of the container so as to be filled with a dose of the powdered medicament, and a triggered state, in which the dosing recess is in communication with the inhalation channel for enabling inhalation of the dose of the powdered medicament contained in the dosing recess through the mouthpiece.

The powder inhaler assembly further comprises:

- an electronic module attached or attachable to the powder inhaler and comprising:
  - a non-contact sensor, optionally an optical proximity sensor, positioned and configured to sense position/s of at least part of the metering device to detect at least when the metering device is in the triggered state.

In a 2$^{nd}$ independent aspect, an electronic module is attached or attachable to a powder inhaler.

The powder inhaler comprises:

- a container for storing a powdered medicament;
- a mouthpiece and an inhalation channel connected to the mouthpiece;
- a metering device having a dosing recess; wherein the metering device is movable, with respect to the container and the inhalation channel, between an idle state, in which the dosing recess is in communication with an opening of the container so as to be filled with a dose of the powdered medicament, and a triggered state, in which the dosing recess is in communication with the inhalation channel for enabling inhalation of the dose of the powdered medicament contained in the dosing recess through the mouthpiece.

The electronic module comprises:

- a non-contact sensor positioned and configured to sense position/s of at least part of the metering device to detect at least when the metering device is in the triggered state; wherein the non-contact sensor is an optical proximity sensor.

In a 3$^{rd}$ independent aspect, a powder inhaler comprises:

- a container for storing a powdered medicament;
- a mouthpiece and an inhalation channel connected to the mouthpiece;
- a metering device having a dosing recess; wherein the metering device is movable, with respect to the container and the inhalation channel, between an idle state, in which the dosing recess is in communication with an opening of the container so as to be filled with a dose of the powdered medicament, and a triggered state, in which the dosing recess is in communication with the inhalation channel for enabling inhalation of the dose of the powdered medicament contained in the dosing recess through the mouthpiece;
- a casing having a respective window; wherein the metering device and optionally the container and the inhalation channel is/are housed in the casing; wherein the metering device is at least in part visible through the window;
- wherein the powder inhaler is configured to be attached to an electronic module comprising an optical proximity sensor;
- wherein when the electronic module is attached to the powder inhaler, the window of the casing faces a window of a housing of the electronic module such that the optical proximity sensor faces at least part of the metering device to sense position/s of said at least part of the metering device in order to detect at least when the metering device is in the triggered state.

The Applicant verified that the invention allows to infer dispensing of a medicament dose in safe and reliable manner by reading the configuration, position and actuation of the mechanical metering device of the powder inhaler through the non-contact sensor. The powder inhaler incorporates a breath actuated mechanism, which is triggered when an inspiratory flow exceeds the minimum required level to move the balanced part of the mechanism, that in turn, releases the metered dose presented in the dosing recess. The actuation is achieved by releasing a sprung component, the coupling member, which then moves a transparent plastic part, called the dose protector forward thus exposing the formulation to the inhalation channel within the mouthpiece. The attached electronic module is configured to detect at least part of this triggering of the mechanism, thus inferring the release of the metered dose. The Applicant verified that the invention allows to perform this detection without imparting relevant structural modification to existing powder inhalers, like, for instance, the one disclosed in WO 2004/012801 or in WO 2016/000983. Indeed, there is no direct access to the internal volume of the powder inhaler.

In an aspect, the electronic module is removably attachable to the powder inhaler, optionally through a clip-on coupling. Coupling and uncoupling is easy and fast.

In an aspect, the electronic module, once detached from a powder inhaler, is reusable with another powder inhaler. The same electronic module may be used with another new powder inhaler once the medicament in an old inhaler is over.

In an aspect, the container is filled or is configured to be filled with an amount of powder medicament corresponding to a plurality of doses, optionally to 100-200 doses.

In an aspect, the non-contact sensor is a proximity sensor. A proximity sensor is a sensor able to detect the presence of nearby objects without any physical contact.

A proximity sensor emits an electromagnetic field or a beam of electromagnetic radiation and looks for changes in the field or return signal. Examples of proximity sensors are capacitive sensors, inductive sensors, optical or photo-electric sensors.

In an aspect, the proximity sensor is an optical proximity sensor.

In an aspect, the optical proximity sensor works in the near-infrared spectrum.

In an aspect, the optical proximity sensor detects changes of reflected electromagnetic waves, optionally light, due to movements of at least part of the metering device.

In an aspect, the powder inhaler comprises a casing, optionally a plastic casing, and the electronic module comprises a housing, optionally a plastic housing.

In an aspect, the housing is removably attachable to the casing, optionally by clipping the housing onto the casing or clipping the casing onto the housing.

In an aspect, the container, the inhalation channel and the metering device are housed in the casing.

In an aspect, the casing has a respective window and the housing has a respective window.

In an aspect, when the electronic module is attached to the powder inhaler, the window of the casing faces the window of the housing such that the optical proximity sensor faces at least part of the metering device.

In an aspect, the optical proximity sensor is placed in the housing.

In an aspect, the window of the casing and the window of the housing are optically transparent windows. Said windows are transparent in the relevant electromagnetic spectra for the optical proximity sensor.

There is no relevant modification the existing inhalers, e.g. the one disclosed in WO 2004/012801 or WO2016/000983, other than a small, optically transparent window that forms part of the outer shell of the inhaler. This window is positioned directly below the part of the mechanism that is triggered by the user's inhalation.

In an aspect, the optical proximity sensor comprises an emitter emitting light, optionally in the near infra-red spectrum, and an optical receiver with a photosensitive part; wherein an output signal of the optical receiver depends on the electromagnetic waves, optionally light, reflected by said at least part of the metering device.

In an aspect, the emitter is a LED (light emitting diode) or a VCSEL (vertical-cavity, surface emitting laser).

In an aspect, the electronic module comprises an electronic control unit, optionally a microprocessor, operatively connected to the non-contact sensor.

In an aspect, the optical proximity sensor or the electronic control unit comprises a lock-in amplifier configured to remove light noise, in particular to remove contribution from external light.

In an aspect, shape and/or size of the window of the casing and/or of the window of the housing are configured to change the field of view (optical mask) of the optical proximity sensor in order to improve detecting the position/s of said at least part of the metering device.

In an aspect, a pinhole sensor cover is interposed between the optical proximity sensor and said at least part of the metering device to change the field of view (optical mask) of the optical proximity sensor in order to improve detecting the position/s of said at least part of the metering device.

In an aspect, at least one lens is interposed between the optical proximity sensor and said at least part of the metering device to better redirect and/or reimage the emitted light and/or the reflected light.

In an aspect, the pinhole sensor cover and/or the at least one lens is part of the electronic module and/or of the powder inhaler.

In an aspect, the electronic module comprises a printed circuit board (PCB).

In an aspect, the electronic module comprises a storage memory.

In an aspect, the electronic module comprises a communication interface, optionally a wireless communication interface, optionally a Bluetooth communication interface.

In an aspect, the communication interface is configured to connect the electronic module to an external device, such as a computer, a smartphone, a tablet or the like. All the working parameters and data of the powder inhaler detected through the electronic module may be transferred to the external device.

In an aspect, the electronic module comprises at least a battery to power on the non-contact sensor, the electronic control unit and the communication interface.

In an aspect, the non-contact sensor, the electronic control unit, the communication interface, the storage memory and the battery are mounted on the printed circuit board.

In an aspect, the electronic control unit is placed in the housing.

In an aspect, the electronic control unit is configured to perform execution of a task comprising at least the following steps:

- reading an output signal from the non-contact sensor at regular intervals;
- optionally, filtering and, optionally, normalizing the output;
- comparing the output with a threshold value and discerning if the metering device is in the triggered state or not.

In an aspect, reading the output signal from the non-contact sensor is performed at a rate greater than 10 Hz, optionally greater than 100 Hz, optionally of 25 Hz (regular intervals less than 100 ms, optionally less than 10 ms, optionally of 40 ms).

In an aspect, the optical components of the optical proximity sensor are only active for a fraction of a millisecond, optionally ranging between 100-300 μs, optionally of 125 μs, and can be considered to take a 'snapshot' of the current position of the metering device at the regular intervals.

In an aspect, a signal processing algorithm is implemented within the electronic control unit to filter the output.

In an aspect, signal processing is performed at least in part by the non-contact sensor.

In an aspect, filtering the output, optionally through the signal processing algorithm, comprises:

- running a median filter on a plurality of samples wherein the median filter output selects an element after sorting the samples in ascending order;
- subtracting the previous median filter output from the current median filter output.

In an aspect, the metering device comprises: a shuttle having the dosing recess. In an aspect, the shuttle is movable between a filling position, corresponding to the idle state of the metering device, in which the dosing recess is in alignment with the opening of the container so as to be filled with the dose of the powdered medicament, and an inhalation position, corresponding at least to the triggered state of the metering device, in which the dosing recess is in alignment with the inhalation channel.

In an aspect, the shuttle is slidingly moveable between the filling position and the inhalation position.

In an aspect, the metering device comprises: a protective member provided between the shuttle and the inhalation channel.

In an aspect, the protective member is moveable between a closed position, in which the protective member covers the dosing recess of the shuttle when the shuttle is in the inhalation position, thereby preventing the powdered medicament contained in the dosing recess from entering into the inhalation channel, and an open position, in which the protective member does not cover the dosing recess, thereby exposing the dosing recess to the inhalation channel so as to enable inhalation of the dose of the powdered medicament contained in the dosing recess. In an aspect, the protective member is arranged on the shuttle slidingly moveable between the closed position and the open position.

In an aspect, the non-contact sensor is positioned and configured to sense position/s of at least the shuttle and/or of the protective member.

In an aspect, in the triggered state, the shuttle is in the inhalation position and the protective member is in the open position.

In an aspect, the metering device is movable, with respect to the container and the inhalation channel, into an armed state, in which the shuttle is in the inhalation position and the protective member is in the closed position.

In an aspect, the non-contact sensor is positioned and configured to sense transition between the armed state and the triggered state.

In an aspect, the powder inhaler comprises an inhalation or breath actuated mechanism coupled to the protective member such that, if the protective member is in the closed position, the inhalation actuated mechanism causes the protective member to move into the open position if an inhalation suction force produced by a user exceeds a predetermined value.

In an aspect, the inhalation actuated mechanism comprises an inhalation actuated member, optionally a flap, being moveable between a first position and a second position; the inhalation actuated member being coupled to the protective member such that, if there is an inhalation suction force exceeding the predetermined value, the inhalation actuated member is moved from the first position to the second position, thereby causing the protective member to move from the closed position to the open position.

In an aspect, the non-contact sensor is positioned and configured to sense position of at least part of the inhalation actuated mechanism.

In an aspect, the optical proximity sensor detects changes of reflected electromagnetic waves, optionally light, due to movements of at least part of the inhalation actuated mechanism.

In an aspect, the inhalation actuated mechanism comprises a coupling member, coupling the inhalation actuated member to the protective member.

In an aspect, the inhalation actuated mechanism comprises at least a resilient element, optionally arranged on the coupling member.

In an aspect, the resilient element is arranged such that the resilient element holds the inhalation actuated member in its first position when the cover is closed and the shuttle is in the filling position.

In an aspect, when the shuttle is pushed forward to the inhalation position by opening the cover, the resilient element releases the inhalation actuated member, so as to allow the inhalation actuated member to be moved from its first position to its second position by an inhalation suction force exceeding the predetermined value.

In an aspect, the coupling member comprises a prolongation engaging with an opening formed in the protective member.

In an aspect, the prolongation of the coupling member is moveably arranged in a longitudinal opening, which is formed in the shuttle along its longitudinal direction, such that the prolongation of the coupling member can freely move in the longitudinal opening of the shuttle from its initial position to its end position, while a movement of the shuttle from the inhalation position to the filling position causes the prolongation of the coupling member to abut against an edge of the longitudinal opening thereby moving the coupling member back into its initial position.

In an aspect, the non-contact sensor is positioned and configured to sense position of at least part of the coupling member, optionally of the prolongation of the coupling member.

In an aspect, the non-contact sensor is positioned and configured to sense position of at least part of the metering device and/or of at least part of the inhalation actuated mechanism.

In an aspect, the optical proximity sensor detects changes of reflected electromagnetic waves, optionally light, due to movements of the shuttle and/or the protective member and/or the coupling member, optionally of the prolongation of the coupling member.

In an aspect, the protective member has a surface reflecting light in a specular fashion and the shuttle has a surface reflecting light diffusely.

In an aspect, the coupling member has a surface reflecting light diffusely.

In an aspect, the protective member has a smooth surface finish reflecting light in a specular fashion (mirror-like reflection), whilst the other two components, the shuttle and the coupling member, reflect light more diffusely, also known as a scattered reflection.

In an aspect, the shuttle and/or the protective member and/or the coupling member has/have at least one marker detectable by the optical proximity sensor.

In an aspect, the marker is part of the shuttle and/or the protective member and/or the coupling member or is an attachment coupled to said shuttle and/or protective member and/or coupling member.

In an aspect, the marker is a diffusely reflecting marker or a specular reflecting marker.

In an aspect, the marker is a diffusely reflecting marker placed on a specular reflecting surface, e.g. the surface of the protective member or of the shuttle.

In an aspect, the marker is a specular reflecting marker placed on a diffusely reflecting surface, e.g. the surface of the coupling member.

In an aspect, the non-contact sensor senses the transition to the triggered state when the light is reflected mainly by the protective member.

In an aspect, the output signal of the optical receiver reaches a maximum when the light is reflected mainly by the protective member.

In an aspect, when the protective member is in the open position, said protective member faces the non-contact sensor.

In an aspect, the overall light received by the optical proximity sensor is governed by the combination of light reflected from all three parts (protective member, coupling member and shuttle) and will be at its maximum when the dominant reflection source is the dose protector. Due to the positioning of the optical proximity sensor, this happens when the powder inhaler's inhalation actuated mechanism is triggered.

In an aspect, the powder inhaler comprises the casing and a cover rotatably coupled to the casing.

In an aspect, the electronic module is attached or attachable onto a portion of the powder inhaler opposite with respect to the cover.

In an aspect, the cover is moveable between a closed position, in which it covers the mouthpiece, and an open position, in which it exposes the mouthpiece.

In an aspect, the electronic module comprises a cover open switch.

In an aspect, the cover open switch is operatively connected to the electronic control unit.

In an aspect, an opening of the cover beyond a range of rotational movement of the cover from the closed position of said cover causes the shuttle to move from the filling position to the inhalation position.

In an aspect, an opening of the cover beyond a range of rotational movement of the cover from the closed position of said cover triggers the cover open switch, which causes activation of the non-contact sensor.

In an aspect, said range of rotational movement is approximately 80 degrees.

In an aspect, closing the cover causes the shuttle to move from the inhalation position to the filling position.

In an aspect, closing the cover releases the cover open switch, which causes deactivation of the non-contact sensor.

In an aspect, the non-contact sensor (and the detection of the state of the metering device) is only active when the cover is open beyond said range of rotational movement.

In an aspect, the cover open switch comprises a mechanical detector switch and a spring-loaded mechanical part, optionally shaped like an arm.

In an aspect, the spring-loaded mechanical part is movable between a rest position, when the cover is in the closed position, in which it does not activate the mechanical detector switch, and a working position, when the cover is in the open position, in which it presses the mechanical detector switch.

In an aspect, a spring is configured to move the spring-loaded mechanical part towards the rest position when the cover is in the closed position.

In an aspect, the electronic module comprises an attachment detection switch interacting with the powder inhaler when the electronic module is attached to the powder inhaler.

In an aspect, the attachment detection switch is mechanical detector switch.

In an aspect, the attachment detection switch is operatively connected to the electronic control unit.

In an aspect, attaching the electronic module to the powder inhaler triggers the attachment detection switch, which causes activation of the cover open switch.

In an aspect, detaching the electronic module from the powder inhaler releases the attachment detection switch, which causes deactivation of the cover open switch.

In an aspect, the closed or open state of the cover is only monitored when the electronic module is attached.

In an aspect, the electronic module uses two mechanical switches to determine, a) when it is attached to the inhaler, and b) when the inhaler's cover is open and therefore an actuation of the internal mechanism may occur.

In an aspect, the electronic module is configured to differentiate between three states:

- the idle state wherein the electronic module is attached to the powder inhaler, the attachment detection switch is triggered, the cover is closed and the cover open switch is released and no inhalation could occur,
- the armed state wherein the cover is open, the cover open switch is triggered and the metering device can be triggered,
- the triggered state wherein an inspiratory flow had released the protective member and a metered dose could be dispensed.

In an aspect, the electronic control unit is configured to store in the storage memory and/or to send to the external device, via the communication interface, data related to events of the powder inhaler, such as, for instance, triggering of the metering device and/or attachment/detachment of the electronic module to/from the powder inhaler and/or opening/closing of the cover.

In an aspect, the electronic control unit is configured first to store said data in the storage memory and then, after a time delay, to send said data to the external device.

In an aspect, the electronic control unit is configured to send, on demand, said data to the external device. Data can be stored only in the electronic control unit as long as a connection with an external device is not available. Therefore, the electronic control unit does not need an external device to properly work and save data.

DETAILED DESCRIPTION

Figures 1, 2:
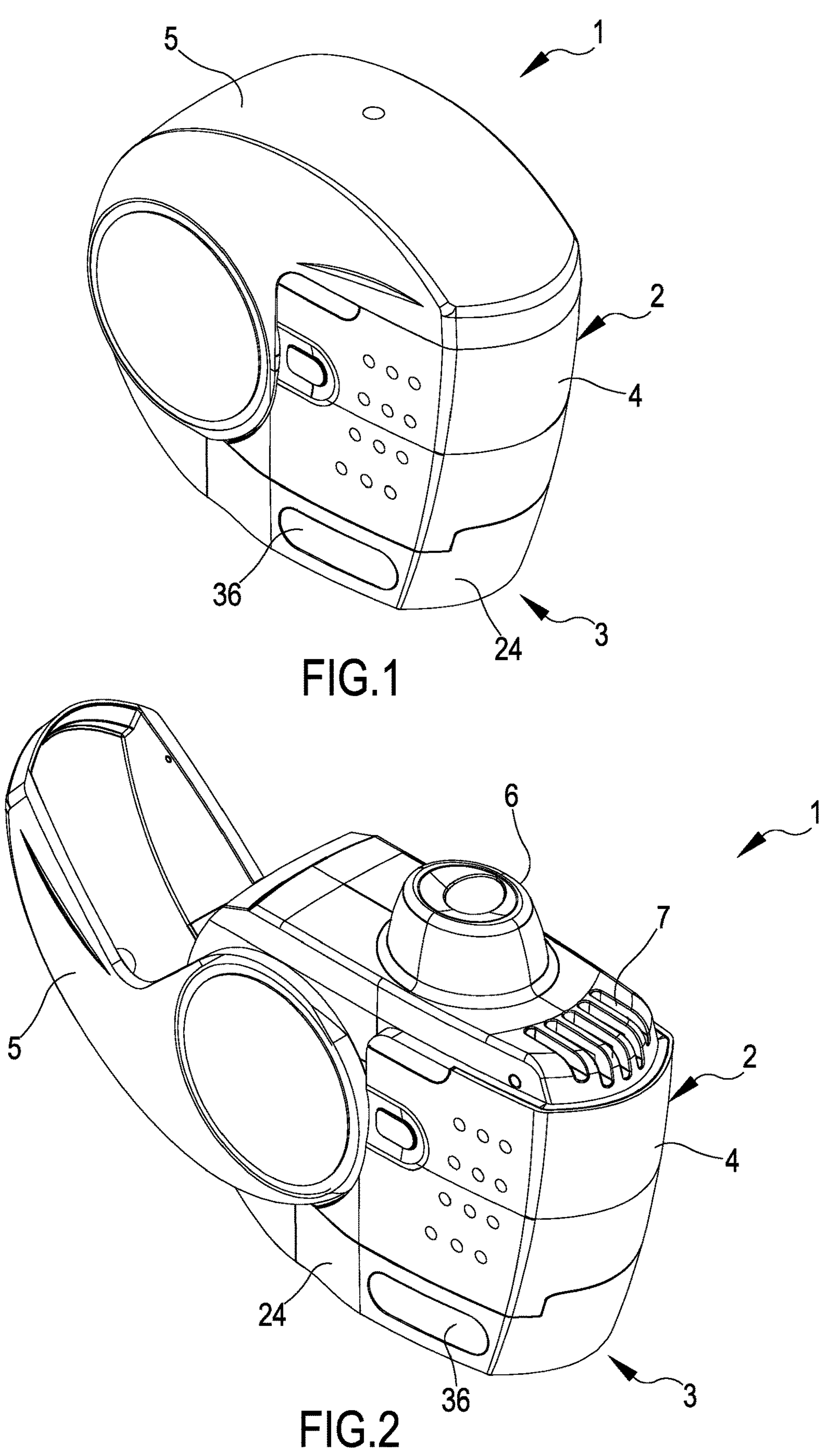
FIG. 1 shows an isometric view of a powder inhaler assembly according to the present invention in a closed configuration.
FIG. 2 shows an isometric view of a powder inhaler assembly according to the present invention in an open configuration.
Figure 3:
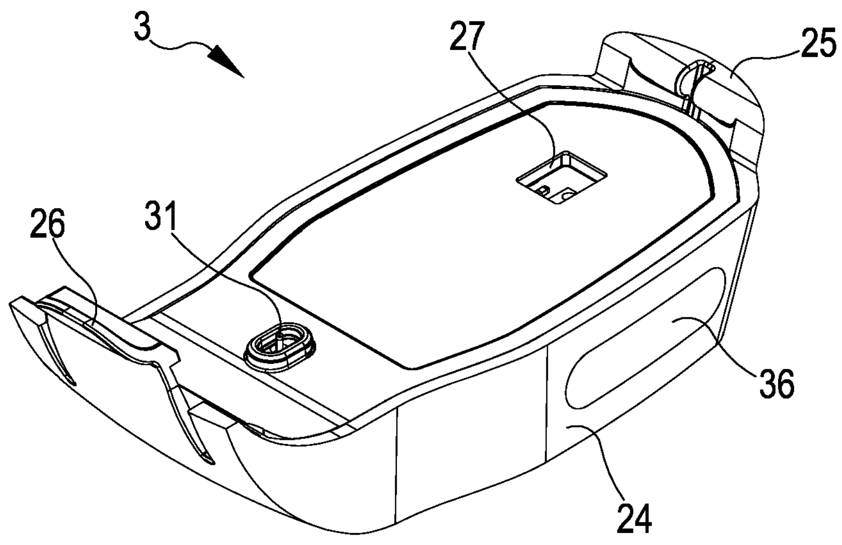
FIG. 3 shows an isometric view of an electronic module of the powder inhaler assembly of FIGS. 1 and 2.
Figure 4:
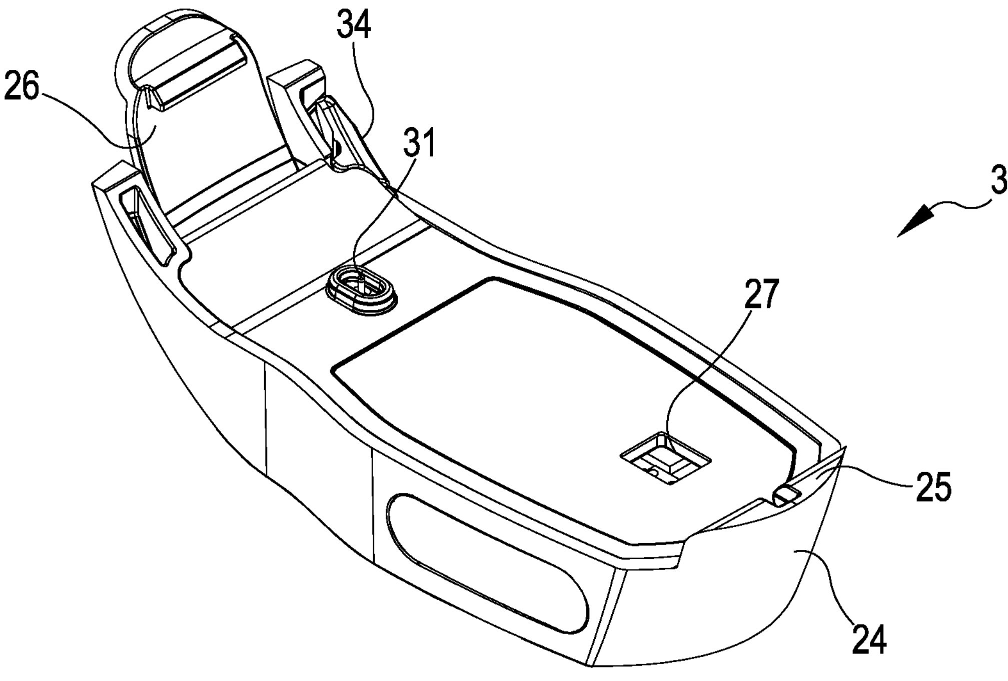
FIG. 4 shows another isometric view of the electronic module of FIG. 3.

With reference to the appended drawings, FIG. 1 and FIG. 2 show a powder inhaler assembly 1 according to the present invention. The powder inhaler assembly 1 comprises a powder inhaler 2 and an electronic module 3. The powder inhaler 2 may be substantially the same as the one disclosed in document WO 2004/012801 or in document WO 2016/000983 of the same Applicant. Therefore, only the main parts and the differences with respect to WO 2004/012801 or WO 2016/000983 will be detailed in the following description.

Powder Inhaler

The powder inhaler 2 shown in FIG. 1 comprises a casing 4 and a cover 5 being pivotably or rotatably coupled to the casing 4. As can be taken from FIG. 2, the cover 5 can be opened to reveal a mouthpiece 6 through which a user can inhale a powdered medicament. At an upper front side of the mouthpiece 6, slots 7 are formed in the casing 4 which allow air inlet.

Figure 5:
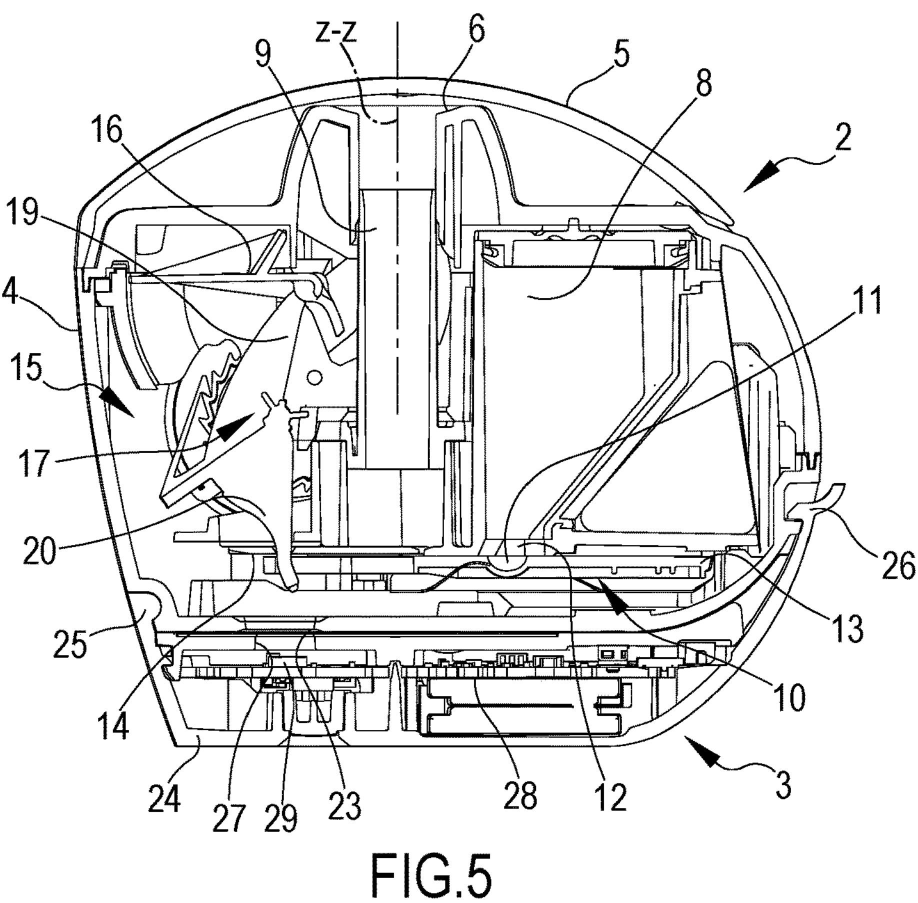
FIG. 5 is a section view of the powder inhaler assembly of the previous figures in a first state.
Figures 7, 8:
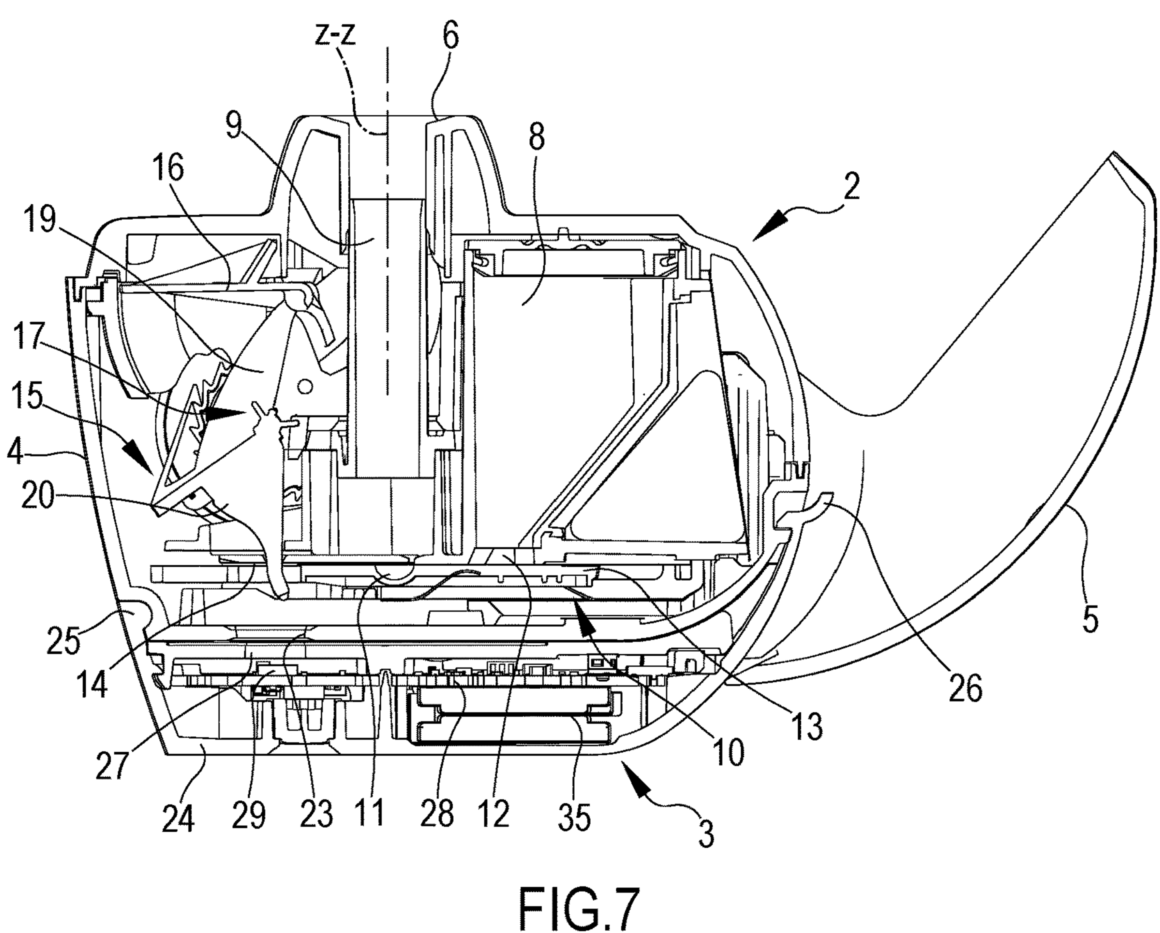
FIG. 7 is a section view of the powder inhaler assembly of the previous figures in a second state.
FIG. 8 is an enlarged portion of FIG. 7.
Figure 9:
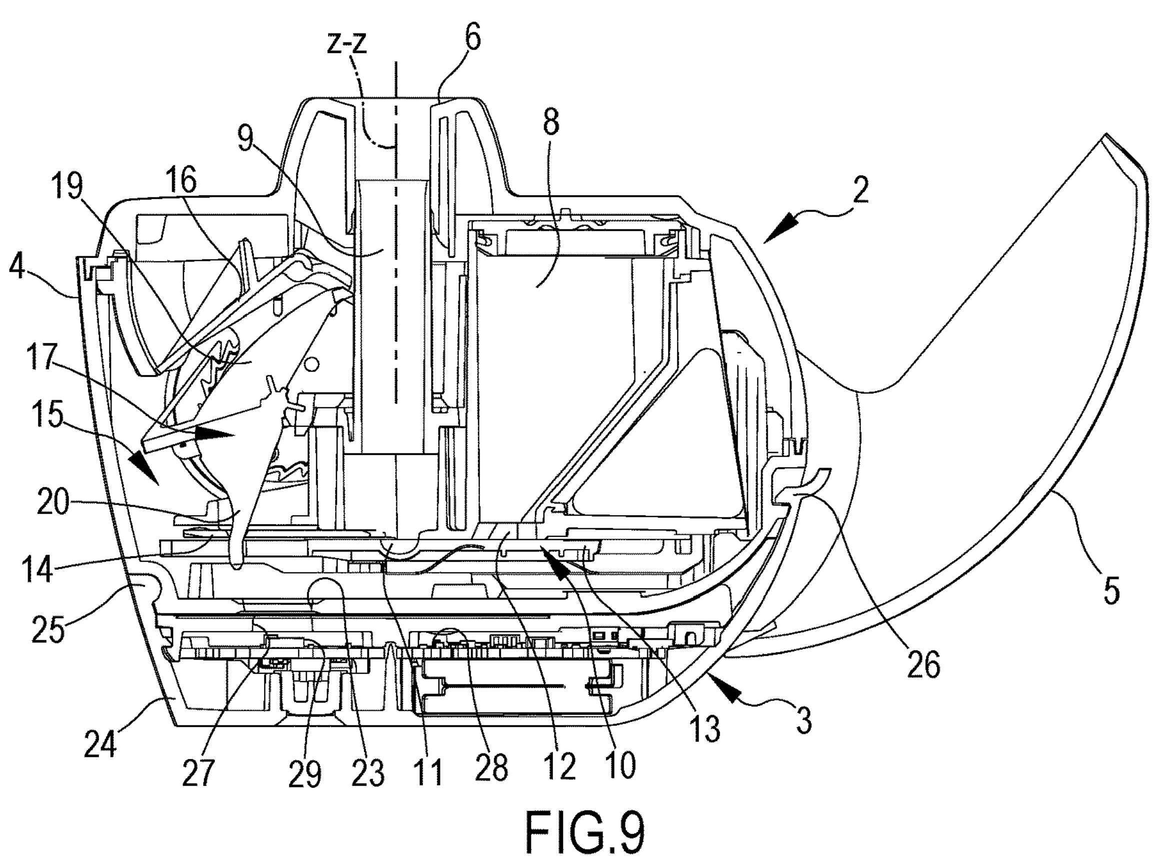
FIG. 9 is a section view of the powder inhaler assembly of the previous figures in a third state.

The powder inhaler 2 comprises a container 8 for storing a powdered medicament, an inhalation channel 9 connected to the mouthpiece 6 and a metering device 10. The inhalation channel 9 has a first opening connected to the mouthpiece and a second opening, opposite with respect to the first opening. As shown in FIGS. 5, 7 and 9, all these elements are housed inside the casing 4.

The container 8 is filled or is configured to be filled with an amount of powder medicament corresponding to a plurality of doses, e.g. up to 100-200 doses.

The metering device 10 is movable, with respect to the container 8 and with respect to the inhalation channel 9, between an idle state, in which a dosing recess 11 is in communication with an opening 12 of the container 8 so as to be filled with a dose of the powdered medicament, and a triggered state, in which the dosing recess 11 is in communication with the inhalation channel 9 for enabling inhalation of the dose of the powdered medicament contained in the dosing recess 11 through the mouthpiece 6.

The metering device 10 comprises a shuttle 13 having the dosing recess 11 fashioned on an upper face like a cup shaped recess. The shuttle 13 is slidingly moveable between a filling position (FIG. 5) and an inhalation position (FIGS. 7 and 9). The filling position corresponds to the idle state (FIG. 5) of the metering device 10, in which the dosing recess is in alignment with the opening 12 of the container 8 so as to be filled with the dose of the powdered medicament. The inhalation position corresponds to an armed state (FIG. 7) which will be detailed later and to the triggered state (FIG. 9) of the metering device 10, in which the dosing recess 11 is in alignment with the inhalation channel 9.

The shuttle 13 is mechanically coupled to the cover 5 such that an opening of the cover 5 beyond a range of rotational movement from the closed position causes the shuttle 13 to move from the filling position to the inhalation position. Closing of the cover 5 causes the shuttle 13 to move back from the inhalation position to the filling position. FIG. 5 shows the cover 5 in the closed position and the shuttle 13 in the filling position. FIGS. 7 and 9 show the cover 5 in an open position and the shuttle 13 in the inhalation position. For instance, the range of rotational movement which causes sliding of the shuttle from the filling position to the inhalation position is eighty degrees.

The metering device 10 further comprises a protective member 14 provided between the shuttle 13 and the inhalation channel 9. The protective member 14 is a transparent or semi-transparent plate arranged between the second opening of the inhalation channel 9 and the shuttle 13. The protective member 14 has a smooth surface finish reflecting light in a specular fashion (mirror-like reflection). The protective member 14 is parallel with respect to the shuttle 13 and is slidingly movable on the shuttle 13 between a closed position and an open position. In the closed position, the protective member 14 is shifted backwards towards the second opening of the inhalation channel 9 and towards the container 8. In the closed position, a rear part of the protective member 14 may at least in part close the second opening of the inhalation channel 9. In the open position, the protective member 14 is shifted forward towards a wall of the casing 4. In the open position, a rear part of the protective member 14 leaves the second opening of the inhalation channel 9 open.

The protective member 14 is in the closed position when the shuttle 13 is in the filling position. The protective member 14 may be moved between the closed position and the open position when the shuttle 13 is in the inhalation position. Therefore, the metering device 10 is configured to take the three different states cited above (idle, armed, triggered) and these states are determined by the positions of the shuttle 13 and of the protective member 14 as disclosed in the following Table 1.

TABLE 1

| State of the metering device | Position of the shuttle | Position of the protective member | FIGS. |
|---|---|---|---|
| Idle | Filling | Closed | 5 and 6 |
| Armed | Inhalation | Closed | 7 and 8 |
| Triggered | Inhalation | Open | 9 and 10 |

Figure 6:
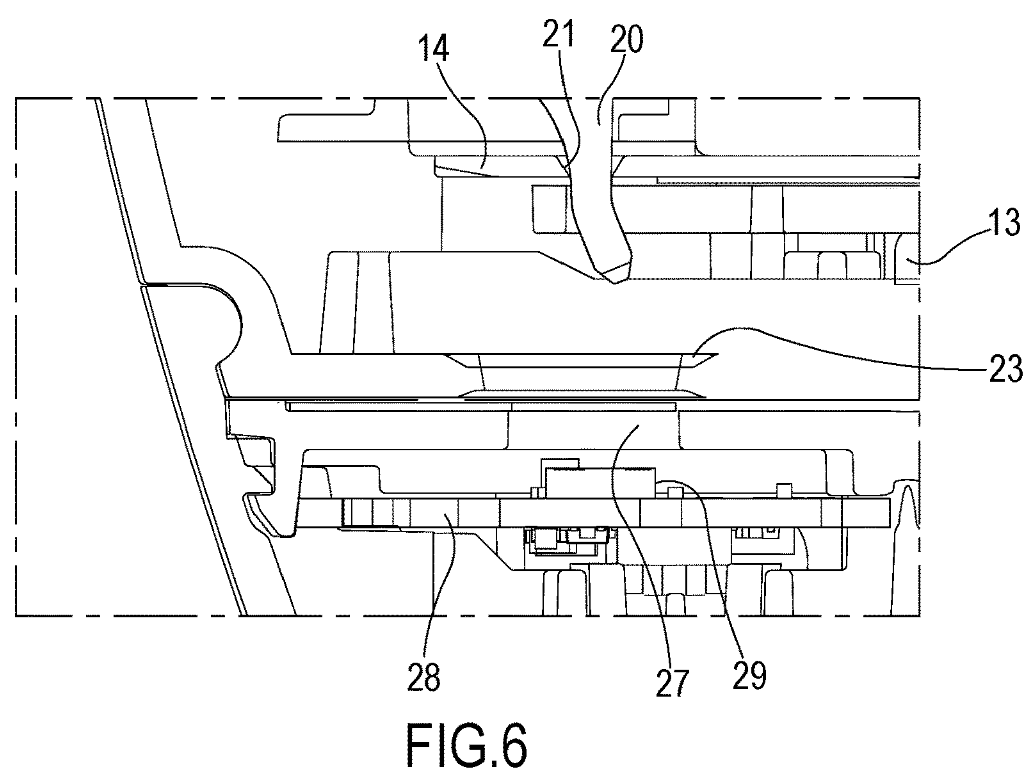
FIG. 6 is an enlarged portion of FIG. 5.

In the idle state of FIGS. 5 and 6, the shuttle 13 is in the filling position and the protective member 14 is in the closed position. The protective member 14 does not cover the dosing recess 11. The dosing recess 11 is communication with the opening 12 of the container 8 to receive the medicament dose.

In the armed state of FIGS. 7 and 8, the shuttle 13 is in the inhalation position and the protective member 14 is in the closed position. The protective member 14 covers the dosing recess 11. The protective member 14 prevents the powdered medicament contained in the dosing recess 11 from entering the inhalation channel 9 and being lost in case of rotation or movement of the inhaler in oblique position before the inhalation maneuver or if the user blows into the mouthpiece.

Figure 10:
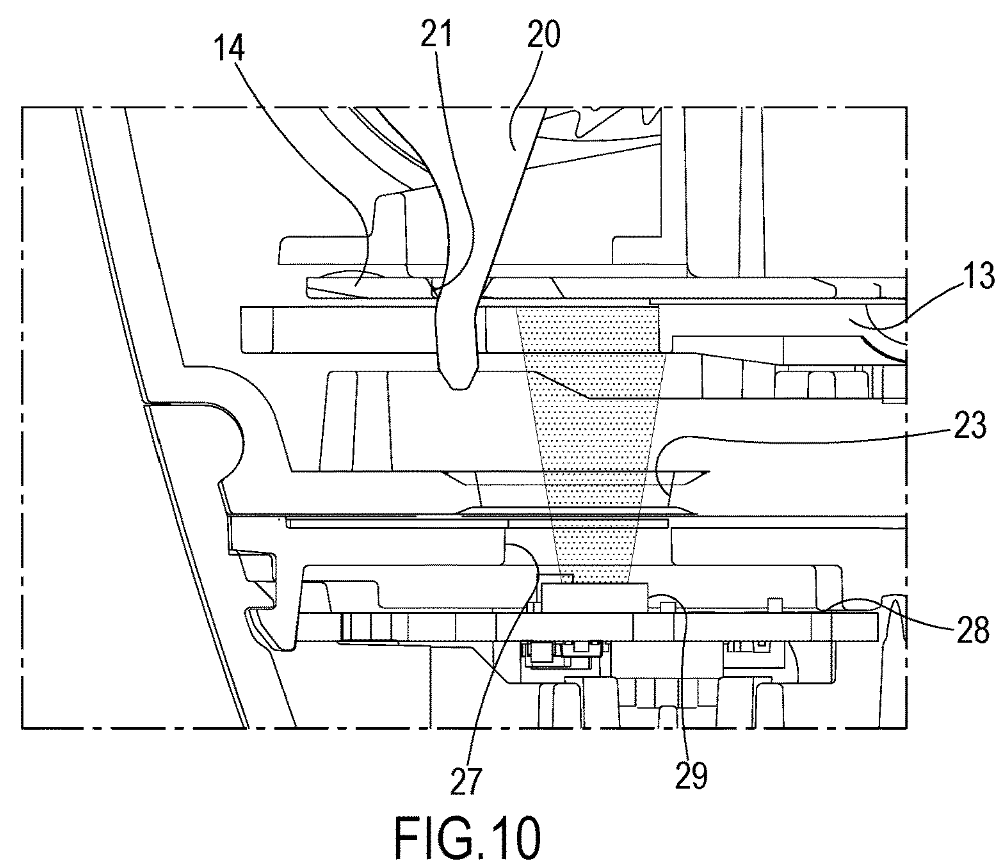
FIG. 10 is an enlarged portion of FIG. 9.

In the triggered state of FIGS. 9 and 10, the shuttle 13 is in the inhalation position and the protective member 14 is in the open position. The protective member 14 does not cover the dosing recess 11, thereby exposing the dosing recess 11 to the inhalation channel 9 so as to enable a user to inhale the dose of the powdered medicament contained in the dosing recess 11.

The powder inhaler 2 comprises a breath or inhalation actuated mechanism 15 coupled to the protective member 14. The inhalation actuated mechanism 15 comprises an inhalation actuated member 16 shaped like a flap, a coupling member 17 and a resilient element 18 arranged on the coupling member 17 (see FIGS. 11, 12 and 13). A further resilient element, not shown in the attached drawings, may be mounted on the coupling member 17 on an opposite side with respect to the resilient element 18 (as in WO 2016/000983). The flap 16 is coupled to the protective member 14 through the coupling member 17 such that, if there is an inhalation suction force exceeding a predetermined value, the flap 16 is moved from a first position to a second position, thereby causing the protective member 14 to move from the closed position to the open position. The flap 16 is placed inside the casing 4 and close to the slots 7. In the first position (FIG. 5), the flap 16 separates the slots 7 from the inhalation channel 9 and seats in a main airflow path. The flap 16 provides a resistance if the user blows into the device giving positive feedback. In the second position (FIG. 9), the flap 16 is rotated with respect to the first position to open the slots 7 and to allow air flowing through the slots 7 into the inhalation channel 9 and out of the mouthpiece 6.

The resilient element 18 is arranged such that said resilient element 18 holds the flap 16 in its first position. When the shuttle 13 is pushed forward by opening the cover 5, the resilient element 18 is compressed and charged and the reset force exerted on the flap 16 is released, so that the flap 16 can pivot or rotate from the first position into the second position that is pivoted downward relative to the first position if there is a sufficient high inhalation suction force in the inhalation channel 9. The further resilient element imparts a suitable force to the coupling member 17 which is released during inhalation. The downward movement of the flap 16 during inhalation releases part of the force exerted by the further resilient element on the coupling member 17, while the closing of the cover 5 tensions the further resilient element.

Figure 11:
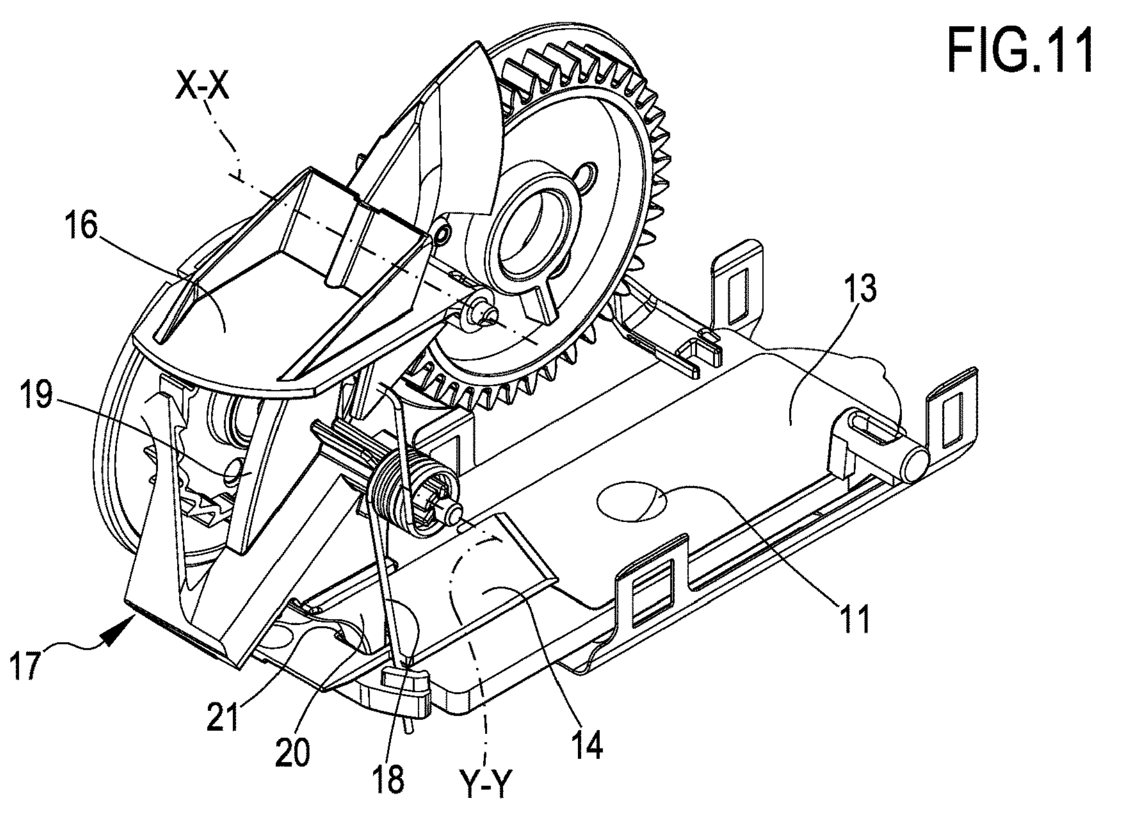
FIG. 11 shows an isometric view of some internal elements of the powder inhaler.
Figure 12:
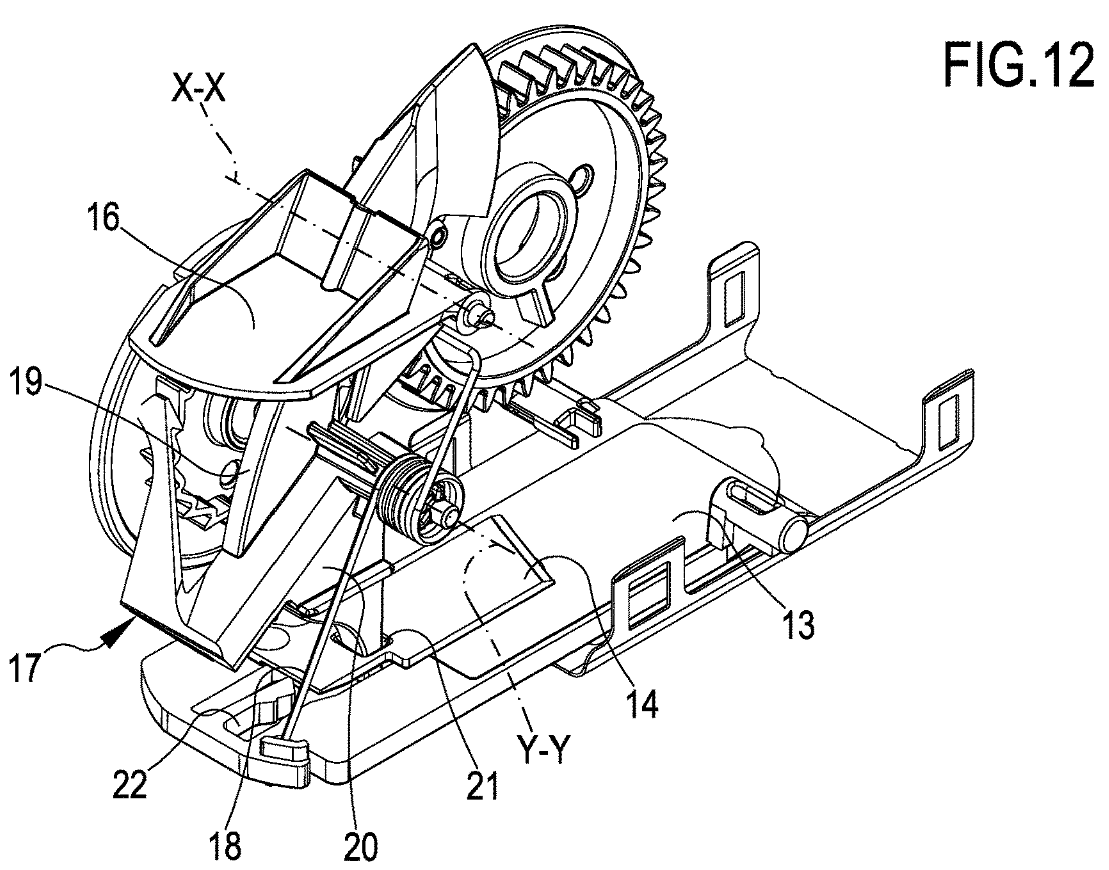
FIG. 12 shows another isometric view of the internal elements of FIG. 11.
Figure 13:
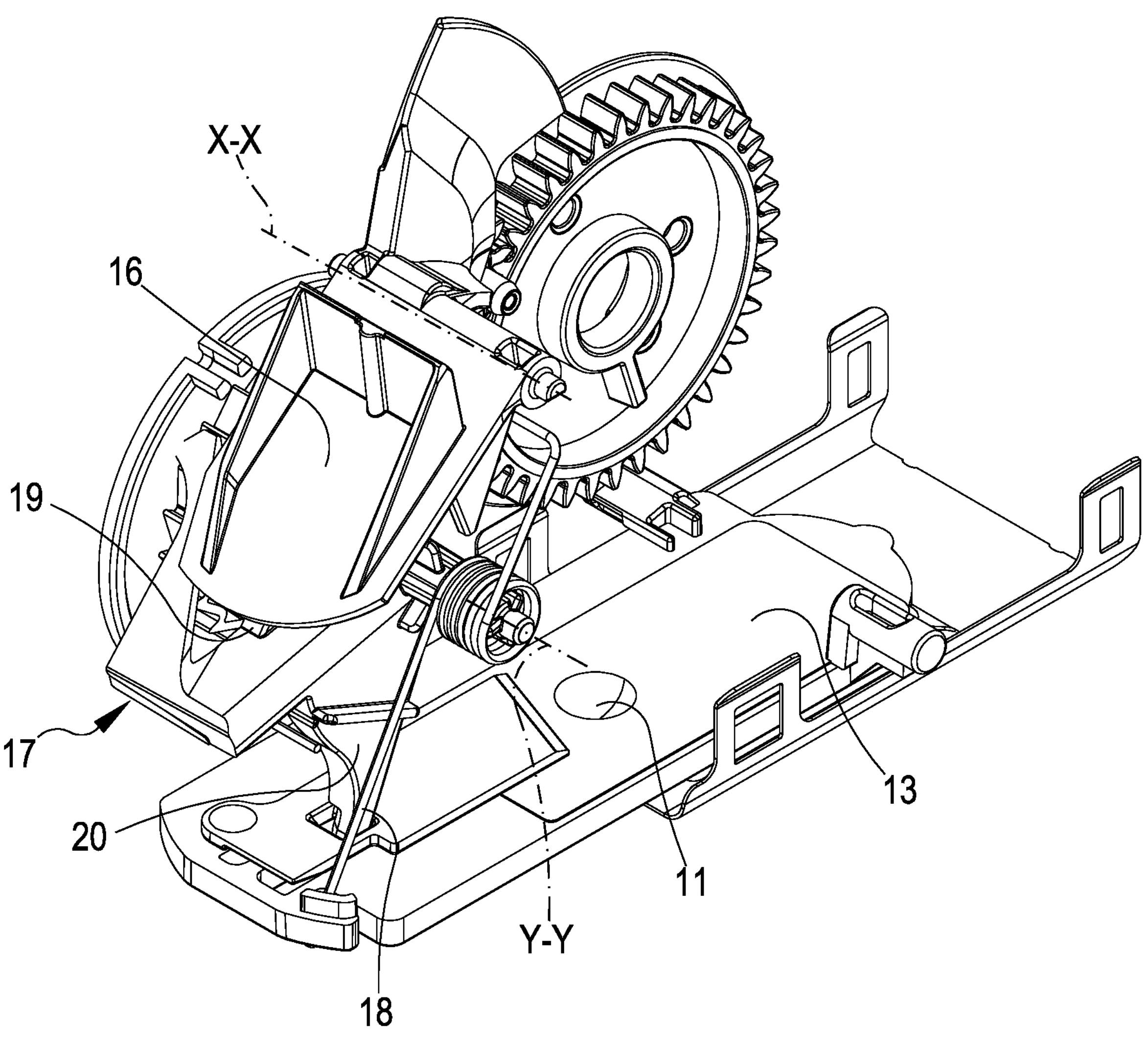
FIG. 13 shows a further isometric view of the internal elements of FIG. 11.
Figure 14:
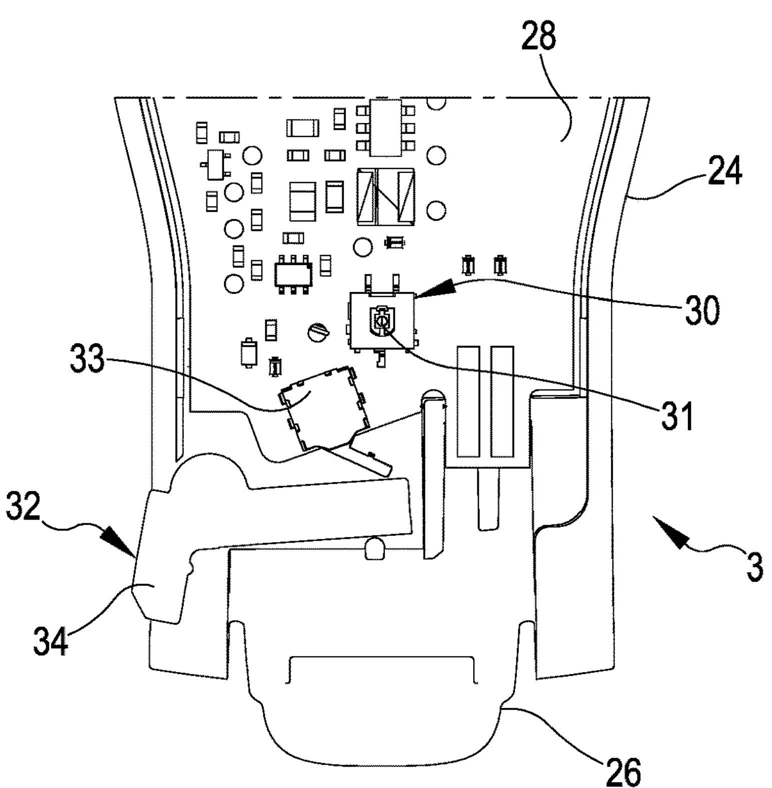
FIG. 14 is a portion of the electronic module in a respective configuration.
Figure 15:
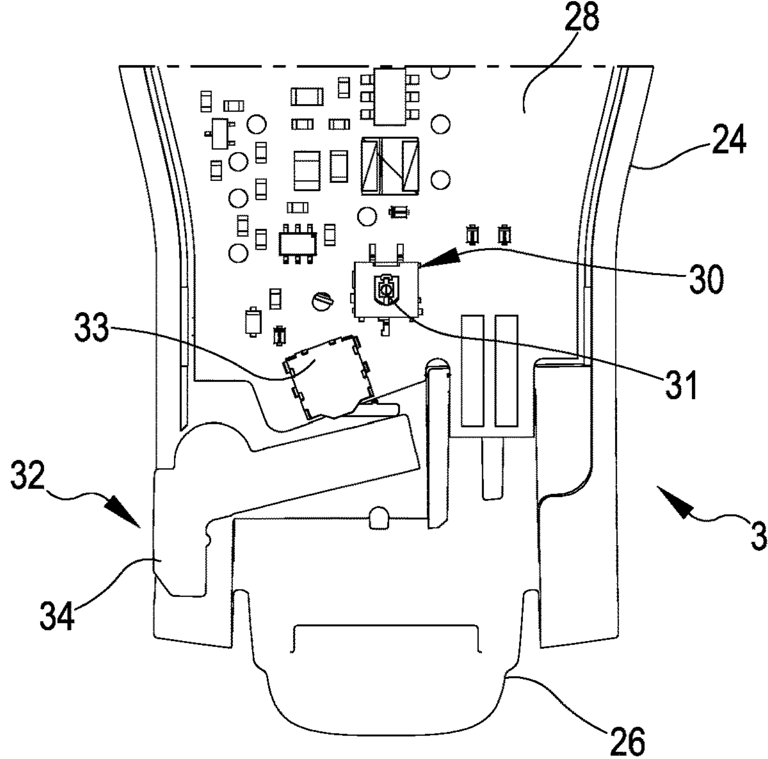
FIG. 15 shows the portion of FIG. 14 in another configuration.

Referring to FIGS. 11 to 13, the flap 16 is hinged to the casing 4 in order to rotate between the first position and the second position around a respective rotation axis X-X which is substantially perpendicular to a main axis Z-Z of the inhalation channel 9 (FIGS. 5, 7 and 9). The coupling member 17 is also hinged to the casing 4 in order to rotate between a respective first position and second position around a respective rotation axis Y-Y which is substantially perpendicular to the main axis Z-Z of the inhalation channel 9 and parallel to rotation axis X-X.

The coupling member 17 comprises an arm 19 protruding towards the flap 16 and engaged with the flap 16 such that (referring to FIGS. 5, 7, 9, 11, 12 and 13) the counterclockwise rotation of the flap 16 from the first position to the second position causes a clockwise rotation of the coupling member 17 from its respective first position towards its respective second position.

The coupling member 17 comprises a prolongation 20 engaging with an opening 21 formed in the protective member 14 in order to move the protective member 14 from the closed position to the open position when the coupling member 17 moves from its respective first position to its respective second position and vice-versa.

The prolongation 20 of the coupling member 17 is also moveably arranged in a longitudinal opening 22 which is formed in the shuttle 13 along its longitudinal direction, such that said prolongation 20 can freely move in the longitudinal opening 22, while a movement of the shuttle 13 from the inhalation position to the filling position causes the prolongation 20 of the coupling member 17 to abut against an edge of the longitudinal opening 22 thereby moving the coupling member 20 back into its initial first position.

The casing 4 has an optically transparent window 23 placed close to the metering device 10 such that the metering device 10 is at least in part visible through the window 23 from outside the casing 4. In particular, the shuttle 13, the protective member 14, and a terminal end of the prolongation 20 are visible through the window 23. While the protective member 14 has a smooth surface finish reflecting light in a specular fashion (mirror-like reflection), the shuttle 13 and the prolongation 20 reflect light more diffusely (scattered reflection). All the elements of the powder inhaler 2 may be made of plastic material.

Electronic Module

The electronic module 3 is configured to be attached in removable manner to the powder inhaler 2 so that the same electronic module 3 may be used with another new powder inhaler 2 once the medicament in the old inhaler is over. In the embodiment shown in the attached Figures, the electronic module 3 is attached or attachable onto a portion of the powder inhaler 2 opposite with respect to the cover 5.

The electronic module 3 comprises a plastic housing 24 removably attachable to the casing 4 of the powder inhaler through a clip-on coupling. The non-limiting embodiment of the housing 24 of the electronic module 3 shown in the attached Figures comprises a rigid clip 25 and a flexible clip 26 shaped to couple with respective recesses of the casing 4 of the powder inhaler 2.

The housing 24 has an upper face configured to face, when the electronic module 3 is attached to the powder inhaler 2, to a lower face of the powder inhaler 2 having the optically transparent window 23. Also, the upper face of the electronic module 3 is provided with a respective optically transparent window 27 and, when the electronic module 3 is attached to the powder inhaler 2, the window 23 of the casing 4 faces the window 27 of the housing 24.

A printed circuit board (PCB) 28 is housed inside the housing 24. The printed circuit board (PCB) 28 carries a microprocessor, a wireless communication interface (e.g. Bluetooth), a storage memory electronically connected one to the other. The communication interface is configured to connect the electronic module to an external device, such as a computer, a smartphone, a tablet or the like. All the working parameters and data of the powder inhaler 2 detected through the electronic module 3 may be stored in the storage memory and/or transferred to the external device.

A non-contact sensor 29 is mounted on the printed circuit board (PCB) 28 and is operatively connected to the microprocessor. The non-contact sensor 29 shown in the attached figures is an optical proximity sensor and comprises an emitter and a receiver side by side. The emitter emits light, e.g. in the near infra-red spectrum, and the receiver is an optical receiver with a photosensitive part. The emitter may be a LED (light emitting diode) or a VCSEL (vertical-cavity, surface emitting laser). The position of the optical proximity sensor 29 on the printed circuit board (PCB) 28 and the position of the printed circuit board (PCB) 28 in the housing 24 is such that the optical proximity sensor 29 is placed in the housing 24 and faces the optically transparent window 27 of said housing 24.

The emitted light and reflected light of the optical proximity sensor 29 pass through the optically transparent window 27 of the housing 24. When the electronic module 3 is attached to the powder inhaler 2, the optical proximity sensor 29 faces the shuttle 13, the protective member 14 and a terminal end of the prolongation 20. An output signal of the optical receiver depends from an amount of light reflected by said parts. The optical proximity sensor 29 is positioned and configured to sense position/s of at least part of the metering device 10 to detect at least when the metering device 10 is in the triggered state. In particular, the optical proximity sensor 29 is positioned and configured to sense position/s of the shuttle 13, of the protective member 14 and of the prolongation 20 of the coupling member 17.

In order assure a proper optical detection of the metering device (in order to better detect signal changes due to the movement of the metering device 10), the shape and/or size of the window 23 of the casing 4 of the powder inhaler 2 and/or of the window 27 of the plastic housing 24 of the electronic module 3 may be configured to change the native field of view (optical mask) of the optical proximity sensor 29. The electronic module 3 further comprises an attachment detection switch 30 interacting with the powder inhaler 2 when the electronic module 3 is attached to the powder inhaler 2. The attachment detection switch 30 is a mechanical detector switch mounted on the printed circuit board (PCB) 28, operatively connected to the microprocessor and comprising a pin 31 protruding from the upper face of the housing 24 through a respective aperture (FIGS. 3, 4, 14 and 15) to mechanically interact with the powder inhaler 2 when the electronic module 3 is attached to the powder inhaler 2.

The electronic module 3 further comprises a cover open switch 32 operatively connected to the microprocessor. The cover open switch 32 comprises (FIGS. 4, 14 and 15) a mechanical detector switch 33 mounted on the printed circuit board (PCB) 28 and operatively connected to the microprocessor and a spring-loaded mechanical part 34 shaped like an arm. A portion of said arm 34 is placed outside the housing 24 of the electronic module 3 to mechanically interact with the cover 5 of the powder inhaler 2 when the cover 5 is opened beyond a range of rotational movement of said cover 5 from the closed position. When the cover 5 is closed, the arm 34 is in a rest position in which it does not activate the mechanical detector switch 33. When the cover 5 is opened beyond said range of rotational movement, the arm 34 is in a work position in which it presses the mechanical detector switch 33. A spring is configured to move the spring-loaded arm 34 towards the rest position when the cover 5 is again in the closed position.

Attaching the electronic module 3 to the powder inhaler 2 triggers the attachment detection switch 30, which causes activation of the cover open switch 32. The closed or open state of the cover 5 is only monitored when the electronic module 3 is attached. The opening of the cover 5 beyond a range of rotational movement of the cover, e.g. eighty degrees, triggers the cover open switch 32, which causes activation of the optical proximity sensor 29. Closing the cover 5 releases the cover open switch 32, which causes deactivation of the optical proximity sensor 29. Detaching the electronic module 3 from the powder inhaler 2 releases the attachment detection switch 30, which causes deactivation of the cover open switch 32.

The electronic module 3 uses the attachment detection switch 30 and the cover open switch 32 to determine, a) when the electronic module 3 is attached to the powder inhaler 2, and b) when the powder inhaler's cover 5 is open and therefore an actuation of the internal mechanism may occur.

The electronic module 3 further comprises a battery 35 mounted on the printed circuit board (PCB) 28 and configured to power on the electronic elements, like the optical proximity sensor 29, the microprocessor, the communication interface, the storage memory, the attachment detection switch 30 and the cover open switch 32. FIGS. 5 and 6 show the electronic module 3 attached to the powder inhaler 2 to form the powder inhaler assembly 1 with the metering device 10 in the idle state, wherein the cover 5 is closed. In the idle state, the attachment detection switch 30 is triggered, the cover open switch 32 is active and the optical proximity sensor 29 is inactive. No light is emitted by the emitter of the optical proximity sensor 29.

FIGS. 7 and 8 show the powder inhaler assembly with the metering device 10 in the armed state, wherein the cover 5 is open. In the armed state, the cover open switch 32 is triggered and the optical proximity sensor 29 is active. The emitter emits a light towards the shuttle 13, the protective member 14 and the terminal end of the prolongation 20. The light is reflected by the shuttle 13, the protective member 14 and the terminal end of the prolongation 20 (reflecting light in scattered fashion) and captured by the optical receiver. The microprocessor reads an output signal from the optical receiver at regular intervals, e.g. at a rate of 25 Hz (every 40 ms). The optical receiver is only active for a fraction of a millisecond, e.g. of 125 μs, and can be considered to take a 'snapshot' of the current position of the metering device at the regular intervals.

The inhalation by the user causes the metering device 10 to move into the triggered state of FIGS. 9 and 10, in which the emitted light hits and is mainly reflected by the protective member 14 (which reflects light in specular fashion) and is then captured by the optical receiver. Once the inhalation actuated mechanism 15 is triggered, it takes approximately 4 ms for the metering device 10 to move from its armed state to its triggered state. This transition is what the optical proximity sensor 29 detects, when the light is reflected mainly by the protective member 14, inferring the triggering of the inhalation actuated mechanism 15.

Figure 16:
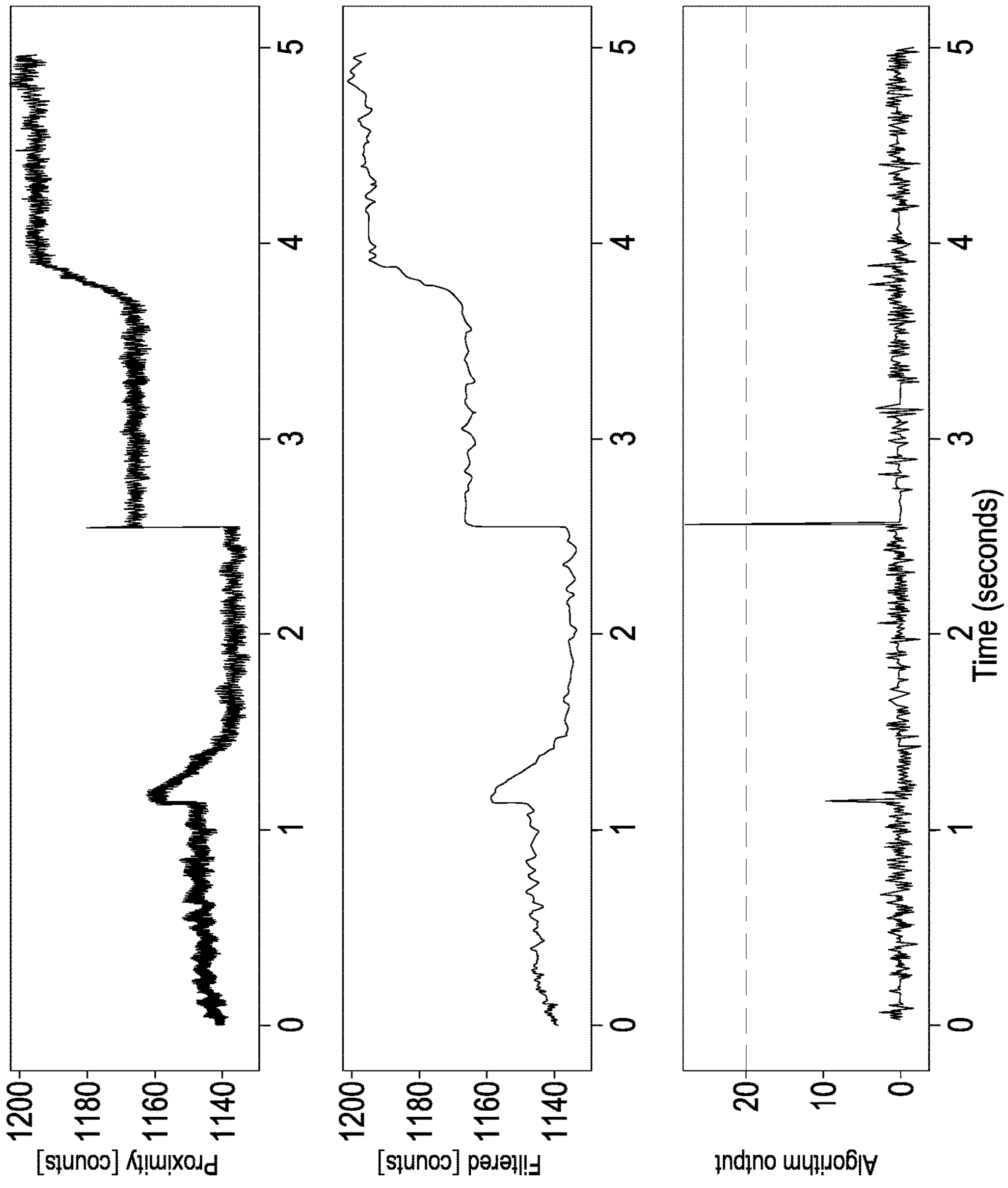
FIG. 16 shows diagrams of a signal relating to the powder inhaler assembly of the previous figures.

An example time-series output from the optical proximity sensor 29 during the triggering of the inhaler's internal mechanism is shown in top graph of FIG. 16. The optical proximity sensor 29 counts that start around 1140 (baseline reading) has a sudden rise around 2.5 s, reaching over 1160, giving a difference in signal levels (contrast) of over 20. Variations in the sensor's output can also be observed at 1.2 s and at 3.8 s in the plots as well due to mechanical forces resulting from manual handling of the powder inhaler assembly, as well as from moving the mouthpiece cover 5 which is directly linked to the shuttle 13 position.

In order to differentiate between these and the signal caused by the state transition of the metering device 10 and of the inhalation actuated mechanism 15, a signal processing algorithm is implemented within the microprocessor. The algorithm can be considered as a type of 'edge-detector' as it is tuned to respond to the fast, positive signal increase caused by the transitional movement of the prolongation 20 of the coupling member 17 and of the protective member 14 as the powder inhaler 2 is triggered to release a metered dose.

The algorithm executes the following task:

- runs a median filter on the last seven samples wherein the median filter output selects the fourth element after sorting the samples in ascending order;
- subtracts the previous median filter output from the current median filter output; this requires a previous valid median filter output to produce a value;
- compares the value obtained above with a threshold and decide "triggered" if the value is greater than the threshold, and "not triggered" otherwise.

FIG. 16 shows the filtered signal (middle graph) as well as the algorithm's output signal over time (lower graph) as a function of the received reflected light. As shown in the lower graph of FIG. 16, the triggering of the inhalation actuated mechanism 15 and of the metering device 10 at approximately 2.5 s on the graph results in a sharp peak of above 20 counts in the algorithm's output which is detected as a successful actuation.

The behaviour described above means that the electronic module 3 can infer a successful release of the metered dose drug formulation if it is attached to the powder inhaler 2 correctly and is actively monitoring the position of the internal mechanisms, primarily the shuttle 13, prolongation 20 and protective member 14, so that it can capture the fast transition that occurs as the inspiratory flow triggers the release of drugs.

The electronic module 3 may be provided with indicators 36, such as LED indicators, operatively connected to the printed circuit board (PCB) 28 and positioned on the housing 24 to be visible by the user. These indicators may provide information regarding the state of the powder inhaler 2. By example, the indicators may signal if the electronic module 3 is correctly attached to the powder inhaler 2 and/or the successful release of the metered dose drug and/or if the electronic module 3 is wirelessly connected to the external device and/or if the cover 5 is open or closed. In some embodiments, not shown, in order to improve optical detection of the moving parts and configurations of the metering device 10, the shuttle 13 and/or the protective member 14 and/or the coupling member 17 has/have at least one diffusely reflecting marker or a specular reflecting marker readily detectable by the optical proximity sensor 29. For instance, a diffusely reflecting marker may be attached to the specular reflecting surface of the protective member 14 in such a way to face the optical proximity sensor 29.

In some other embodiments, not shown, the position of the optical proximity sensor 29 with respect to the metering device 10 may be other than the one shown in FIGS. 5 to 10, so that also the detected parts or parts of the metering device 10 may be different. Referring to FIG. 6, 8 or 10, the optical proximity sensor 29 may be placed a little more to the left on the printed circuit board (PCB) 28. In one embodiment, when the metering device 10 is in the armed state, the emitted light hits and is mainly reflected by the clear protective member 14 (which reflects light in specular fashion) and, when the metering device 10 is in the triggered state, the emitted light hits and is mainly reflected by the diffusely reflecting marker of the protective member 14. In one embodiment, when the metering device 10 is in the armed state, the emitted light hits and is mainly reflected by the clear protective member 14 (which reflects light in specular fashion) and, when the metering device 10 is in the triggered state, the emitted light hits and is mainly reflected by the coupling member 17 (which reflects light in scattered fashion). In one embodiment, when the metering device 10 is in the armed state, the emitted light hits nothing and, when the metering device 10 is in the triggered state, the emitted light hits and is mainly reflected by the diffusely reflecting marker of the protective member 14.

In some other embodiments, not shown, between the optical proximity sensor 29 and said at least part of the metering device 10, a pinhole sensor cover (cover provided with a tiny aperture) and/or at least one lens, not shown, may be interposed. The pinhole sensor cover and/or the lens may be located in the plastic housing 24 of the electronic module 3 or in the casing 4 of the powder inhaler 2. These elements may be useful to better detect signal changes due to the movement of the metering device 10.

The pinhole sensor cover is adopted to change the native field of view (optical mask) of the optical proximity sensor 29 (in addition or in place of the shape and/or size of the window 23 of the casing 4 and/or of the window 27 of the plastic housing 24). The lens is used to redirect and/or reimage the emitted light and/or the reflected light. The emitted light may be better focused on the target part of the metering device 10. The reflected light may be better reimaged on the optical receiver.

The optical proximity sensor 29 or the electronic control unit of other embodiments may comprise a lock-in amplifier configured to remove noise, in particular to remove the noise due to the contribution from light signals outside the casing (e.g. ambient light). A lock-in amplifier is per se known and is a type of amplifier that can extract a signal with a known carrier wave from a noisy environment.

The invention claimed is:

1. A powder inhaler assembly, comprising:

a powder inhaler comprising:

a container for storing a powdered medicament;

a mouthpiece and an inhalation channel connected to the mouthpiece;

a casing and a cover rotatably coupled to the casing so that the cover is moveable between a closed position, in which the cover covers the mouthpiece, and an open position, in which the cover exposes the mouthpiece; and a metering device having a dosing recess; wherein the metering device is movable, with respect to the container and the inhalation channel, between an idle state, in which the dosing recess is in communication with an opening of the container so as to be filled with a dose of the powdered medicament, an armed state, in which the cover is open, and a triggered state, in which the dosing recess is in communication with the inhalation channel for enabling inhalation of the dose of the powdered medicament contained in the dosing recess through the mouthpiece; and an electronic module attached or attachable to the powder inhaler and configured to differentiate between the idle state, the armed state, and the triggered state, the electronic module comprising:

an electronic control unit;

a cover open switch operatively connected to the electronic control unit; and a proximity sensor operatively connected to the electronic control unit;

wherein the proximity sensor is positioned and configured to sense a transition between the armed state and the triggered state by sensing a position position/s of at least part of the metering device.

2. The assembly according to claim 1, wherein the electronic module comprises a housing; wherein the metering device and the container and the inhalation channel is/are housed in the casing; wherein the casing has a respective window and the housing has a respective window; wherein, when the electronic module is attached to the powder inhaler, the window of the casing faces the window of the housing such that the proximity sensor faces at least part of the metering device.

3. The assembly according to claim 2, wherein the proximity sensor is an optical proximity sensor working in the near-infrared spectrum, and the window of the casing and the window of the housing are optically transparent windows.

4. The assembly according to claim 3, wherein the metering device comprises:

a shuttle having the dosing recess, wherein the shuttle is movable between a filling position, corresponding to the idle state of the metering device, in which the dosing recess is in alignment with the opening of the container so as to be filled with the dose of the powdered medicament, and an inhalation position, corresponding at least to the triggered state of the metering device, in which the dosing recess is in alignment with the inhalation channel;

a protective member provided between the shuttle and the inhalation channel, the protective member being moveable between a closed position, in which the protective member covers the dosing recess of the shuttle when the shuttle is in the inhalation position, thereby preventing the powdered medicament contained in the dosing recess from entering into the inhalation channel, and an open position, in which the protective member does not cover the dosing recess, thereby exposing the dosing recess to the inhalation channel so as to enable inhalation of the dose of the powdered medicament contained in the dosing recess;

wherein the optical proximity sensor is positioned and configured to sense position/s of the shuttle and/or of the protective member.

5. The assembly according to claim 4, wherein the metering device is movable, with respect to the container and the inhalation channel, into the armed state, in which the shuttle is in the inhalation position and the protective member is in the closed position.

6. The assembly according to claim 4, wherein the powder inhaler comprises an inhalation actuated mechanism [coupled to the protective member such that, if the protective member is in the closed position, the inhalation actuated mechanism causes the protective member to move into the open position if an inhalation suction force being produced by a user exceeds a predetermined value; wherein the optical proximity sensor is positioned and configured to sense position(s) of at least part of the inhalation actuated mechanism.

7. The assembly according to claim 6, wherein the inhalation actuated mechanism comprises an inhalation actuated member and a coupling member coupling the inhalation actuated member to the protective member, the optical proximity sensor being positioned and configured to sense position of at least part of the coupling member.

8. The assembly according to claim 7, wherein the optical proximity sensor is configured to detect changes of reflected light due to movements of the shuttle and/or the protective member and/or the coupling member.

9. The assembly according to claim 4, wherein, when the protective member is in the open position, said protective member faces the optical proximity sensor.

10. The assembly according to claim 1, wherein the electronic control unit is operatively connected to the proximity sensor, wherein the electronic control unit and/or the proximity sensor are configured to perform execution of a task comprising at least the following steps:

reading an output signal from the proximity sensor at regular intervals;

filtering the output;

comparing the output with a threshold value and discerning if the metering device is in the triggered state or not.

11. The assembly according to claim 1, wherein an opening of the cover beyond a range of rotational movement of the cover from the closed position of said cover causes the shuttle to move from the filling position to the inhalation position and triggers the cover open switch which causes activation of the proximity sensor; wherein closing the cover causes the shuttle to move from the inhalation position to the filling position and releases the cover open switch which causes deactivation of the proximity sensor.

12. The assembly according to claim 11, wherein the electronic module comprises an attachment detection switch interacting with the powder inhaler when the electronic module is attached to the powder inhaler; wherein attaching the electronic module to the powder inhaler triggers the attachment detection switch which causes activation of the cover open switch; wherein detaching the electronic module from the powder inhaler releases the attachment detection switch which causes deactivation of the cover open switch.

13. The assembly according to claim 1, wherein the electronic module is removably attachable to the powder inhaler through a clip-on coupling.

14. The assembly according to claim 1, wherein the electronic module comprises a storage memory, wherein the electronic control unit is configured first to store data in the storage memory and then, after a time delay, to send said data to an external device.

15. A powder inhaler assembly, comprising:

a powder inhaler comprising:

a container for storing a powdered medicament;

a mouthpiece and an inhalation channel connected to the mouthpiece;

a casing and a cover rotatably coupled to the casing so that the cover is moveable between a closed position, in which the cover covers the mouthpiece, and an open position, in which the cover exposes the mouthpiece; and a metering device having a dosing recess; wherein the metering device is movable, with respect to the container and the inhalation channel, between an idle state, in which the dosing recess is in communication with an opening of the container so as to be filled with a dose of the powdered medicament, an armed state, in which the cover is open, and a triggered state, in which the dosing recess is in communication with the inhalation channel for enabling inhalation of the dose of the powdered medicament contained in the dosing recess through the mouthpiece; and an electronic module removably attachable to the powder inhaler and configured to differentiate between the idle state, the armed state, and the triggered state, the electronic module comprising:

an electronic control unit:

a cover open switch operatively connected to the electronic control unit; and an optical proximity sensor operatively connected to the electronic control unit;

wherein the proximity sensor is positioned and configured to sense a transition between the armed state and the triggered state by sensing a position of at least part of the metering device;

wherein the electronic module further comprises a housing;

wherein the metering device is housed in the casing and the optical proximity sensor is located in the housing;

wherein the casing has a respective window and the housing has a respective window;

wherein, when the electronic module is attached to the powder inhaler, the window of the casing faces the window of the housing such that the optical proximity sensor faces the at least part of the metering device.

16. The assembly according to claim 15, the optical proximity sensor comprising an emitter, wherein the emitter is a light emitting diode (LED) or a vertical-cavity surface emitting laser (VCSEL).

17. The assembly according to claim 15, wherein a pinhole sensor cover is interposed between the optical proximity sensor and said at least part of the metering device to change the field of view of the optical proximity sensor.

18. The assembly according to claim 15, wherein at least one lens is interposed between the optical proximity sensor and said at least part of the metering device to redirect and/or reimage emitted light and/or reflected light.

19. The assembly according to claim 15, wherein the metering device comprises:

a shuttle having the dosing recess, wherein the shuttle is movable between a filling position, corresponding to the idle state of the metering device, in which the dosing recess is in alignment with the opening of the container to be filled with the dose of the powdered medicament, and an inhalation position, corresponding at least to the triggered state of the metering device, in which the dosing recess is in alignment with the inhalation channel; and a protective member between the shuttle and the inhalation channel, the protective member configured to move between a closed position, in which the protective member covers the dosing recess of the shuttle when the shuttle is in the inhalation position, thereby preventing the powdered medicament contained in the dosing recess from entering into the inhalation channel, and an open position, in which the protective member does not cover the dosing recess, thereby exposing the dosing recess to the inhalation channel to enable inhalation of the dose of the powdered medicament contained in the dosing recess;

wherein the optical proximity sensor is positioned and configured to sense position/s of the shuttle and/or of the protective member;

wherein the protective member has a surface reflecting light specularly and the shuttle has a surface reflecting light diffusely or wherein the shuttle and/or the protective member has/have at least one marker detectable by the optical proximity sensor.

20. The assembly according to claim 19, wherein the electronic module is removably attachable onto a portion of the powder inhaler opposite the cover.

* * * * *